United States Patent
Clifton et al.

(10) Patent No.: US 12,226,452 B2
(45) Date of Patent: Feb. 18, 2025

(54) POLYHEDRIN-BASED SLOW RELEASE GROWTH FACTOR SYSTEM FOR NEUROPROTECTION OF RETINAL GANGLION CELL NEURONS

(71) Applicants: The Schepens Eye Research Institute, Inc., Boston, MA (US); Cell Guidance Systems Ltd, Cambridge (GB)

(72) Inventors: Julia Oswald Clifton, Medford, MA (US); Christian Pernstich, Cambridge (GB); Petr Baranov, Boston, MA (US); Michael Jones, Royston (GB)

(73) Assignees: The Schepens Eye Research Institute, Inc., Boston, MA (US); Cell Guidance Systems Ltd, Cambridge (GB)

( * ) Notice: Subject to any disclaimer, the term of this patent is extended or adjusted under 35 U.S.C. 154(b) by 48 days.

(21) Appl. No.: 17/192,328

(22) Filed: Mar. 4, 2021

(65) Prior Publication Data
US 2021/0275638 A1  Sep. 9, 2021

Related U.S. Application Data

(60) Provisional application No. 62/985,196, filed on Mar. 4, 2020.

(51) Int. Cl.
*A61K 38/18* (2006.01)
*A61P 27/06* (2006.01)

(52) U.S. Cl.
CPC ............ *A61K 38/185* (2013.01); *A61P 27/06* (2018.01)

(58) Field of Classification Search
CPC ........ A61K 38/185; A61K 38/18; A61P 27/06
See application file for complete search history.

(56) References Cited

U.S. PATENT DOCUMENTS

| | | | |
|---|---|---|---|
| 6,261,545 B1 * | 7/2001 | Okamoto ............ | A61K 38/185 514/913 |
| 7,432,347 B2 | 10/2008 | Ohta et al. | |
| 7,619,060 B2 | 11/2009 | Ikeda | |
| 8,554,493 B2 * | 10/2013 | Metcalf ................ | C07K 14/475 703/11 |
| 2007/0260203 A1 * | 11/2007 | Donello ................. | A61P 27/06 424/428 |
| 2020/0277570 A1 | 9/2020 | Matsuzaki et al. | |

FOREIGN PATENT DOCUMENTS

| WO | WO-2006056823 A1 * | 6/2006 | ......... A61K 38/1866 |
|---|---|---|---|

OTHER PUBLICATIONS

Miltner et al., "Retinal Ganglion Cell Replacement: Current Status and Challenges Ahead," Developmental Dynamics, Published online Oct. 11, 2018, 248: 118-128. (Year: 2018).*

Almasieh & Levin, "Neuroprotection in Glaucoma: Animal Models and Clinical Trials," Annual Review of Vision Science, Sep. 2017, 3:91-120.
Carelli et al., "Optic neuropathies: the tip of the neurodegeneration iceberg," Hum. Mol. Genet., Oct. 2017, 26(R2): R139-R150.
Chang et al., "An engineered three-dimensional stem cell niche in the inner ear by applying a nanofibrillar cellulose hydrogel with a sustained-release neurotrophic factor delivery system," Acta Biomaterialia, May 2020, 108:111-127.
Doozandeh & Yazdani, "Neuroprotection in Glaucoma," Journal of Ophthalmic & Vision Research, Apr. 2016, 11(2):209-220.
Eiraku and Sasai, "Mouse embryonic stem cell culture for generation of three-dimensional retinal and cortical tissues," Nature Protocols, Jan. 2012, 7(1): 69-79.
Harper et al., "Transplantation of BDNF-Secreting Mesenchymal Stem Cells Provides Neuroprotection in Chronically Hypertensive Rat Eyes," Invest Ophthalmol. Vis. Sci., Jun. 2011, 52(7):4506-4515.
Ikeda et al., "Molecular characterization of Bombyx mori cytoplasmic polyhedrosis virus genome segment 4," J. Virol., Jan. 2001, 75(2):988-995.
Matsumoto et al., "Bone regeneration by polyhedral microcrystals from silkworm virus," Sci. Rep., Dec. 2012, 2(1):935, 7 pages.
Matsuzaki et al., "Sustained neurotrophin release from protein nanoparticles mediated by matrix metalloproteinases induces the alignment and differentiation of nerve cells," Biomolecules, Oct. 2019, 9(10):510.
Mori et al., "Expression of Bombyx mori cytoplasmic polyhedrosis virus polyhedrin in insect cells by using a baculovirus expression vector, and its assembly into polyhedra," J. Gen. Virol., Jan. 1993, 74(1):99-102.
Mori et al., "Nucleotide Sequence of the Polyhedrin Gene of Bombyx mori Cytoplasmic Polyhedrosis Virus A Strain with Nuclear Localization of Polyhedra," J. Gen. Virol., 1989, 70 70(7):1885-1888.
Nishishita et al., "The use of leukemia inhibitory factor immobilized on virus-derived polyhedra to support the proliferation of mouse embryonic and induced pluripotent stem cells," Biomaterials, May 2011, 32(14):3555-3563.
Nucd et al., "Neuroprotective agents in the management of glaucoma," Eye, May 2018, 32(5):938-945.
Occhiutto et al., "Nanotechnology for medical and surgical glaucoma therapy—a review," Adv. Ther., Jan. 2020, 37(1):155-199.
Oswald al., "Modulation of host microenvironment by sustained growth factor delivery enhances donor RGC morphology following allotransplantation," Abstract, Presented at ARVO 2020 Annual Meeting, Baltimore, MD, Available Online Jun. 12, 2020; Investigative Ophthalmology & Visual Science, 61(7):660, 2 page.
Rusciano et al., "Neuroprotection in Glaucoma: Old and New Promising Treatments," Advances in Pharmacological Sciences, 2017, Article ID 4320408, 19 pages.
Weinreb et al., "The pathophysiology and treatment of glaucoma: a review," JAMA., May 2014, 311(18):1901-1911.
www.cellgs.com [online], "PODS® proteins," Sep. 2011, retrieved on May 17, 2021, retrieved from URL<https://www.cellgs.com/services/pods-proteins/>, 2 pages.

(Continued)

*Primary Examiner* — Julie Ha
(74) *Attorney, Agent, or Firm* — Fish & Richardson P.C.

(57) ABSTRACT

Described herein are polyhedrin-based slow release growth factor systems and methods of use thereof for neuroprotection of host and donor retinal ganglion cell neurons.

14 Claims, 5 Drawing Sheets

Specification includes a Sequence Listing.

(56) References Cited

OTHER PUBLICATIONS

Zhao et al., "Polylactic-co-glycolic acid microspheres containing three neurotrophic factors promote sciatic nerve repair after injury," Neural Regen. Res., Sep. 2015, 10(9):1491-1497.

* cited by examiner

POLYHEDRIN-BASED SLOW RELEASE GROWTH FACTOR SYSTEM FOR NEUROPROTECTION OF RETINAL GANGLION CELL NEURONS

CLAIM OF PRIORITY

This application claims the benefit of U.S. Provisional Application Ser. No. 62/985,196, filed on Mar. 4, 2020. The entire contents of the foregoing are incorporated herein by reference.

FEDERALLY SPONSORED RESEARCH OR DEVELOPMENT

This invention was made with Government support under Grant No. EY029893 awarded by the National Institutes of Health. The Government has certain rights in the invention.

TECHNICAL FIELD

Described herein are polyhedrin-based slow release growth factor systems and methods of use thereof for neuroprotection of host and donor retinal ganglion cell neurons.

BACKGROUND

Optic neuropathies, including glaucoma, are a group of neurodegenerative diseases characterized by the progressive loss of retinal ganglion cells (RGCs) leading to irreversible vision loss.

SUMMARY

Described herein are compositions and methods for treating an optic neuropathy associated with neurodegeneration in the eye and loss of retinal ganglion cells (RGCs). The methods include administering to an affected eye of the subject a therapeutically effective amount of a composition comprising complexes of one or more growth factors attached to polyhedra comprising polyhedrin protein.

In some embodiments, the growth factors comprise one, two, or all three of human Brain-derived neurotrophic factor (BDNF), Glial cell line-derived neurotrophic factor (GDNF), and/or Ciliary neurotrophic factor (CNTF).

In some embodiments, the growth factors have an N-terminal tag that facilitates attachment to the polyhedrin. In some embodiments, the N terminal tag comprises an H1-tag that comprises an N-terminus H1 helix of a polyhedrin protein or a VP3 tag comprising a region of a capsid protein VP3 of cytoplasmic polyhedrosis virus. In some embodiments, the H1-tag comprises Met Ala Asp Val Ala Gly Thr Ser Asn Arg Asp Phe Arg Gly Arg Glu Gln Arg Asn Ser Glu Gln Tyr Asn Tyr Asn Ser Ser (SEQ ID NO:1).

In some embodiments, the subject has glaucoma, diabetic retinopathy/RGC loss in diabetes, Leber's hereditary optic neuropathy (LHON), toxic optic neuropathy, nonarteritic anterior ischaemic optic neuropathy (NAION), ischemic optic neuropathy, or retrograde degeneration associated with a pathology involving the Central Nervous System (CNS).

In some embodiments, the subject has early-stage glaucoma, diabetic retinopathy/RGC loss in diabetes, LHON, toxic optic neuropathy, NAION, ischemic optic neuropathy, or retrograde degeneration associated with a pathology involving the CNS. In some embodiments, the subject retains at least 30%, 40%, 50%, 60%, 70%, 80%, or 90% of the normal Retinal Nerve Fiber Layer (RNFL) thickness assessed by optical coherence tomography (OCT).

In some embodiments, the subject has late stage glaucoma, diabetic retinopathy/RGC loss in diabetes, LHON, toxic optic neuropathy, NAION, ischemic optic neuropathy, or retrograde degeneration associated with a pathology involving the CNS. In some embodiments, the subject retains less than 10%, 20%, 30%, 40%, or 50%, of the normal Retinal Nerve Fiber Layer (RNFL) thickness assessed by optical coherence tomography (OCT).

In some embodiments, the methods also include administering a population of donor RGCs to the subject.

In some embodiments, the donor RGCs are derived from iPSC generated from cells from the subject or universal HLA-matched donor iPSC.

In some embodiments, the composition is administered by intravitreal or subretinal injection.

In some embodiments, the pathology of the CNS is Alzheimer's disease, Parkinson's disease, or demyelinating optic neuritis.

In some embodiments, the subject is human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Blindness and vision impairments resulting from the loss or degeneration of retinal ganglion cells (RGCs) are irreversible. While the underlying pathology of optic neuropathies (ON) is diverse (e.g., elevation of intraocular pressure, acute trauma), all phenotypically resemble neurodegenerative disease. From an initial decrease in the visual field, congruent with dyschromatopsia and changes in the pupillary response, patients gradually progress towards a complete loss of vision. Optical coherence tomography and other live imaging approaches have shown that retinal ganglion cell death in glaucoma is a slow process, thus it is possible to preserve the remaining function and, potentially, reverse some of the vision loss with timely application of pro-survival factors. Several pro-survival and anti-apoptotic pathways have been utilized as therapeutic targets in glaucoma, including ERk, p38, PTEN, JNK and others. Multiple growth factors and small molecules have been tested, including Brain-Derived Neurotrophic Factor (BDNF) and Glial Cell Derived Neurotrophic Factor (GDNF). They have shown profound neuroprotective properties in vitro in primary retinal neuron cultures and in vivo in acute models of neuron death. However, traditional challenges associated with the delivery of recombinant proteins remain unsolved. These include quick clearance from the vitreous and insufficient bioavailability at the target cell niche, resulting in the need for regular repeated injections.

Several slow-release formulations of these growth factors (e.g., Zhao et al., Neural Regen Res. 2015 September; 10 (9): 1491-1497); Harper et al., Invest Ophthalmol Vis Sci. 2011 June; 52 (7): 4506-4515; and Occhiutto et al., Adv Ther. 2020; 37 (1): 155-199)) have been tested and showed some promise in animal models of optic neuropathy in rescuing rod and bipolar function and preventing RGC death. However, none of them achieved functional rescue of RGCs as measured by scotopic threshold response or have made it to clinical trial for glaucoma.

Growth Factor-Polyhedrin Protein Complexes

Provided herein are slow-release compositions that include complexes of a cargo protein comprising a growth factor (such as human BDNF, GDNF, and/or CNTF) that is attached to a micron-sized proteinaceous particle, known as polyhedra, for zero-order sustained-release of the growth factor. The polyhedra comprise or consist of polyhedrin protein derived from polyhedrosis virus. In some embodiments, the growth factors have an N-terminal tag that facilitates attaching to the polyhedrin, e.g., comprising a region of a capsid protein VP3 of cytoplasmic polyhedrosis virus, more specifically, a region which is either a region from the N-terminus to the 40th amino acid residue or a region from the 41st amino acid residue to the 79th amino acid residue as an embedding signal for polyhedron (see U.S. Pat. Nos. 7,619,060 and 7,432,347). In some embodiments, the growth factors have an N-terminal tag (e.g., an H1-tag that comprises an N-terminus H1 helix of a polyhedrin protein or functional equivalent thereof, preferably comprising Met Ala Asp Val Ala Gly Thr Ser Asn Arg Asp Phe Arg Gly Arg Glu1 Gln Arg Asn Ser Glu Gln Tyr Asn Tyr Asn Ser Ser (SEQ ID NO:1); see, e.g., U.S. Pat. No. 8,554,493). Polyhedrin proteins useful in the present compositions are known in the art, and include those described in U.S. Pat. Nos. 7,619,060, 7,432,347, and 8,554,493; US2020/0277570; and Mori et al., J. Gen. Virol., (1989), 70 (Pt 7): 1885-1888; Mori et al., J. Gen. Virol., (1993) 74:99-102; Ikeda et al., J. Virol., (2001), 75:988-995. A commercially available system, e.g., the POlyhedrin Delivery System (PODS®) (Cell Guidance Systems LLC, St. Louis MO USA), can also be used. See also Matsuzaki et al., Biomolecules 2019, 9 (10), 510 (nerve growth factor (NGF)-polyhedra); Chang et al., Acta Biomaterialia, May 2020, 108:111-127 (BDNF-polyhedra).

Exemplary sequences for the growth factor cargo proteins are as follows:

Human BDNF Amino Acid Sequence:

(SEQ ID NO: 2)
MADVAGTSNRDFRGREQRLFNSEQYNYNNSKNSRPSTSLYKKAGLMHSDP

ARRGELSVCDSISEWVTAADKKTAVDMSGGTVTVLEKVPVSKGQLKQYFY

ETKCNPMGYTKEGCRGIDKRHWNSQCRTTQSYVRALTMDSKKRIGWRFIR

IDTSCVCTLTIKRGR

Human GDNF Amino Acid Sequence:

(SEQ ID NO: 3)
MADVAGTSNRDFRGREQRLFNSEQYNYNNSKNSRPSTSLYKKAGLMSPDK

QMAVLPRRERNRQAAAANPENSRGKGRRGQRGKNRGCVLTAIHLNVTDLG

LGYETKEELIFRYCSGSCDAAETTYDKILKNLSRNRRLVSDKVGQACCRP

IAFDDDLSFLDDNLVYHILRKHSAKRCGCI

Human CNTF Amino Acid Sequence:

(SEQ ID NO: 4)
MAFTEHSPLTPHRRDLCSRSIWLARKIRSDLTALTESYVKHQGLNKNINL

DSADGMPVASTDQWSELTEAERLQENLQAYRTFHVLLARLLEDQQVHFTP

TEGDFHQAIHTLLLQVAAFAYQIEELMILLEYKIPRNEADGMPINVGDGG

LFEKKLWGLKVLQELSQWTVRSIHDLRFISSHQTGIPARGSHYIANNKKM

The sequences used can be at least 80, 85, 90, 95, or 100% identical to the exemplary (reference) sequences provided herein, but should retain the desired activity of the exemplary (reference) sequence. Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 60% (e.g., at least 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a BLOSUM 62 scoring matrix with a gap penalty of 12, a gap extend penalty of 4, and a frameshift gap penalty of 5.

Growth factor-polyhedrin protein complexes can be made using methods known in the art; see, e.g., Mori et al., J. Gen. Virol. 74 (1), 99-102 (1993); U.S. Pat. Nos. 7,619,060, 7,432,347, and 8,554,493. In some embodiments, cargo protein expression, folding and incorporation into polyhedrin crystals are achieved within insect cells, e.g., *Spodop-*

*tera frugiperda* IPLB-SF21-AE cells (Sf21) or Sf9 cells (a clonal isolate of *Spodoptera frugiperda* Sf21 cells), but other cells (e.g., insect cells S2, Tni and others) can also be used. Capturing the nascent cargo protein and embedding them into growing polyhedrin crystals ensures bioactivity; these robust polyhedrin crystal-protein complexes are then harvested and purified. This production process is in contrast to producing conventional growth factors, where expressed growth factor protein is purified by subjecting it to a series of purification steps and columns.

Methods of Use

Described herein are methods using growth factors delivered using polyhedrin-based particles (e.g., PODS). The methods can be used to treat optic neuropathies associated with neurodegeneration in the eye and loss of RGCs, including glaucoma, diabetic retinopathy/RGC loss in diabetes, Leber's hereditary optic neuropathy (LHON), dominant optic atrophy (DOA), nonarteritic anterior ischaemic optic neuropathy (NAION), ischemic optic neuropathy, and retrograde degeneration associated with pathologies involving the Central Nervous System (e.g., Alzheimer's disease, Parkinson's disease, and demyelinating optic neuritis). See, e.g., Carelli et al., Hum Mol Genet. 2017 Oct. 1; 26 (R2): R139-R150. Subjects who have loss of RGCs and can be treated using the present methods can be identified by a skilled health care provider, e.g., using ophthalmoscopic examination of the optic nerve head, Visual Field Test, optic nerve head photographs, confocal scanning laser ophthalmoscopy, scanning laser polarimetry, and Retinal Nerve Fiber Layer (RNFL) thickness assessed by optical coherence tomography (OCT). See, e.g., Weinreb et al., JAMA. 2014 May 14; 311 (18): 1901-1911.

Generally, the methods include administering a composition comprising a therapeutically effective amount of one or more growth factors linked to PODS as described herein, to an eye of a subject who is in need of, or who has been determined to be in need of, such treatment. In some embodiments, the methods include administering the composition directly to the eye of the subject, e.g., by intravitreal or subretinal injection.

As used in this context, to "treat" means to ameliorate at least one symptom of the disorder associated with loss of RGCs. These conditions result in loss of vision; thus, a treatment comprising or consisting of administration of a therapeutically effective amount of a composition described herein can result in a reduction in rate or extent of RGC loss and a return or approach to normal vision (e.g., with an associated improvement in neuronal structure and/or function), or a preservation of existing vision (e.g., with associated preservation of neuronal structure and/or function). In some embodiments, the subject has an early stage of the disease, and the present methods slow or reduce risk of progression.

In some embodiments, e.g., where neuronal loss is more extensive, the methods can include co-administration of RGCs, e.g., autologous RGS developed from induced pluripotent stem cells, e.g., using methods of ESC/iPSC-derived retinal cell differentiation. Such methods are known in the art, e.g., using three-dimensional retinal organoids. See, e.g., the methods described herein and Eiraku and Sasai, Nature Protocols, 2012. 7:69-79. RGCs can be subsequently dissociated from the organoids and isolated, e.g., by fluorescence activated cell sorting (FACS) or magnetic microbead sorting (MMBS), based on surface antigens, e.g., Thy1 (CD90.2) or L1cam (CD171), before transplantation. In some embodiments, prior to transplantation, the iPSC-derived RGCs are maintained in culture for at least 20 or 21 days, or until subtype-specific molecular markers, e.g., Osteopontin, Kcng4, and/or Melanopsin, are expressed. These methods can include one or more subretinal or intravitreal injections of cells (e.g., $10^4$ or $10^5$-$10^6$ or more cells per injection).

Examples

The invention is further described in the following examples, which do not limit the scope of the invention described in the claims.

Materials and Methods

The following materials and methods were used in the Examples below.

Pods Production.

All PODS® proteins were synthesized as previous described (Nishishita et al., Biomaterials 32, 3555-3563 (2011); Matsumoto et al., Sci. Rep. 2, 935 (2012). All constructs were fused to the H1 incorporation tag. Briefly, baculovirus (BV) DNA and transfer DNA was co-transfected into standard *Spodoptera frugiperda* 9 (Sf9) cells using TransIT®-Insect (Mirus Bio). The resulting infective BV was harvested, and a plaque purification then performed to isolate a single recombinant BV. Isolated plaques were first screened, expanded and finally used to infect large scale Sf9 cells cultures to produce PODS® crystals. Subsequently, crystals were harvested and purified by lysing Sf9 cells using successive rounds of sonication and PBS washes. Finally, purified PODS® were sterility tested and lyophilized prior to use in experiments.

Cell Culture and Retinal Tissue Differentiation.

The Thy1-GFP+ mouse iPSC used for the presented data were originally derived from Tg(Thy1-eGFP)M mouse fibroblasts by overexpression of the Oct4-Sox2-Klf4-CMyc cassette. For maintenance miPSC were stored in liquid nitrogen and thawed for plating on Matrigel(Corning)-coated flasks at 2,000 cells/cm2 in mESC medium (for culture media content—see Table 1). Pluripotency was confirmed in miPSC by Flow Cytometry prior to organoid formation. For organoid seeding miPSC were collected with Trypsin-EDTA as single cell suspension, washed through single centrifugation at 250 g for 4 min and resuspended in Optic Vesicle (OV) medium. For spheroid formation 1.500 cells in 50 μl of OV medium were plated in low-adhesion V-bottom 96-well plates and incubated at 37° C. After 24 hrs, an equal volume of 2% Matrigel in OV medium was added to induce forebrain/retinal differentiation. Spheroids were cultured in OV medium with 1% Matrigel for 8 days and then transferred to Optic Cup (OC) medium.

Subsequently, organoids were kept in OC medium for additional 7 or 12 days (day 16 and day 21 total, respectively), with half media changes every 3 days, for retinal maturation. Beyond day 14 of culture organoids were structurally stable to be transferred from 96-well plates into petri dishes for maintenance. Differentiation batch quality was confirmed by morphological assessment and Thy1-GFP expression respectively prior to subsequent experimentation.

TABLE 1

Media Composition and Methods

ESC maintenance medium (mES medium):

500 ml DMEM/F12 (or GMEM)
5 ml 100x Glutamax (or L-Glutamine)

TABLE 1-continued

Media Composition and Methods 5 ml 100x antibiotic-antimycotic solution
5.5 ml 100x non-essential amino acids (MEM NEAA)
5.5 ml 100x sodium pyruvate
4 ul 16M b-Mercaptoethanol
50 ul 100 ug/ml mLIF
65 ml of HI FBS
Filter, store at +4, use within a month.
Optic vesicle medium (OV medium):

500 ml DMEM/F12 (or GMEM)
5 ml 100x Glutamax (or L-Glutamine)
5.1 ml 100x non-essential amino acids
5.1 ml 100x sodium pyruvate
5.1 ml 100x antibiotic-antimycotic solution
5.1 ml 100x Lipid concentrate
1 ml ITS-X supplement
7.6 ml HI FBS
1.25 ml of NAC stock (2.5 uL/ml in HBSS)
4 ul 16M b-Mercaptoethanol
Filter, store at +4, use within a month.
Optic cup medium (OC medium):

500 ml DMEM/F12 (or GMEM)
5 ml 100x Glutamax (or L-Glutamine)
5.1 ml 100x non-essential amino acids
5.1 ml 100x sodium pyruvate
5.1 ml 100x Lipid concentrate
5 ml 100x antibiotic-antimycotic solution
4 ul 16M b-Mercaptoethanol
10 ml NS21 (50x)
1.25 ml of NAC stock (2.5 uL/ml in HBSS)
Filter, store at +4, use within a month.

PODS Treatment of In-Vitro Organoid Cultures.

PODS treatment was initiated congruent with the transition of organoids from 96-well plates into petri dishes and is maintained until RGCs are isolated. While most commonly organoids are transferred at day 14 of culture, application of PODS has been tested as early as day 9 of culture, congruent with the transition from OV to OC media if RGCs are subsequently isolated at day 21 of culture. Dependent on the concentration of PODS and duration of overall culture, we also found success with late treatment between day 20 to day 30 of culture. PODS are measured as particles to determine concentration and $50 \times 10^6$ PODS can be equated to 3.3 μg of conventional, recombinant protein. In our study we have employed a range of 80,000 to 160,000 PODS per ml of media in-vitro; estimating an overall effective concentration range from between 25,000 to 250,000 PODS per ml. PODS are adherent to plastic surfaces and therefore withstand subsequent media exchange; meaning that over the treatment timeframe they are only applied once.

Organoid Dissociation.

Before dissociation, 0.1 mg/ml of papain was dissolved in fresh activation buffer (1.1 mM EDTA, 0.3 mM beta-mercaptoethanol and 5.5 mM cysteine-HCl). The solution was filtered through a 0.22 μm filter and incubated for 30 min within a 37° C., 5% $CO_2$ incubator. Meanwhile organoids were manually collected and washed with HBSS. After removal of the supernatant, activated papain solution (10 ml of solution for every 3×96 organoids) was added to the organoids and incubated for up to 15 min under occasional manual swirling within an 37° C., 5% $CO_2$ incubator. After incubation, 3 ml of FBS was added per 10 ml of papain mixture to stop digestion and cells were centrifuged for 5 min at 300 g. After supernatant removal, cells were resuspended in OC medium and counted.

RGC Isolation Via FACS or Magnetic Microbead Sorting (MMBS).

For FACS, dissociated cells were resuspended in cold IsoFlow Sheath Fluid and passed through a 70 μm mesh. Sorting was performed in liquid droplets, using a Cytomation MOFLO Cell Sorting setup at a sheet fluid pressure of 25-30 psi. Magnetic microbead sorting for Thy1.2+ cells was performed according to the manufacturer protocol using the Dynabeads™ Mouse Pan T (ThermoFisher) kit, with isolation buffer including both BSA and FBS as stated within the manual. To improve cell purity, bead bound cells ware washed twice prior to bead release. In contrast to FACS, which specifically isolates Thy1-GFP+ RGCs, magnetic microbeads directly target the Thy1.2 (CD90.2) surface antigen, crosslinking Thy1-expressing cells to magnetic microbeads, allowing for the enrichment of both, GFP+ Thy1+ and GFP- Thy1+ cells.

Transplantation Studies.

All animal studies were performed according to the Association for Research in Vision and Ophthalmology (ARVO) guidelines. The animal protocol was approved by the Schepens Eye Research IACUC. For transplantation Thy1-GFP+ cells were isolated at day 22 of differentiation by FACS or MMBS and formulated as 10,000 viable cells per microliter in OC medium. Intravitreal injections into 1 to 3 months old adult mice were performed under general anesthesia (ketamine/xylazine). In addition to the healthy adults, mice with NMDA-induced neurotoxicity were used as hosts. In these hosts, RGC death was induced at one week prior to cell transplantation by NMDA injection (2 μl of 20 mM NMDA were injected intravitreally). The loss of host RGC death was confirmed by RBPMS staining in retinal whole mount preparations. Immediately prior to the injections proparacaine drops were applied for local anesthesia to the eye. In adults 2 μl of cell suspension was delivered into the vitreous or subretinal space through a beveled glass microneedle (80 μm inner diameter). PODS were added to donor cells or injected by themselves in a volume of 2 ul; at a concentration of 150 PODS/ul equivalent to 150.000 PODS/ml a dose comparable to those used in-vitro. Following donor cell injection, a triple antibiotic ointment was applied. Injection success could be confirmed in some animals in-vivo using Micron III Imaging at 2-weeks post-transplantation. Animals were sacrificed at the experimental end point by CO2 inhalation with death being confirmed by cervical dislocation. Eyes were subsequently enucleated, fixed in 4% paraformaldehyde for 48 hrs and then processed for sectioning or retinal whole mount preparation.

Tissue Preservation, Immunohistochemistry and Confocal Microscopy.

For immunohistochemistry of whole mounts, samples were first placed in blocking buffer (10% goat serum, 1% BSA, 0.1% sodium citrate, 0.1% tween 20, 0.1% triton-x in 1×PBS) for 2 hrs and subsequently incubated with primary antibody in staining buffer (1% BSA, 0.1% tween 20, 0.1% triton-x in 1×PBS) at 4° C. for 48 hrs. To remove unbound primary antibody samples were washed 3×15 min with washing buffer (0.1% tween 20, 0.1% triton-x in 1×PBS). Alexa secondary antibodies at 1:500 dilution were applied in staining solution for 3 hrs at RT followed by 2×15 min wash steps. Samples were then incubated in DAPI (400 ng/ml, Sigma Aldrich) and rinsed in PBS prior to mounting with glycerol-PVA based mounting medium. All microscopy pictures were obtained from a Leica TCS-SP5 Upright Confocal Laser-Scanning Microscope. A list primary antibodies used in this study can be found in the Table 2.

TABLE 2

Antibodies used for Immunohistochemistry.

| ANTIGEN | DILUTION | SPECIES | CAT., SUPPLIER |
|---|---|---|---|
| B3-tubulin | 1:500 | mouse | T8660, Sigma Aldrich |
| GFP | 1:1000 | chicken | ab 13970, Abcam |
| RBPMS | 1:400 | rabbit | ab 194213, Abcam |

BDNF ELISA

50 µl of a PBS solution containing either 1e6, 5e5, 2e5, 5e4 or 1e4 PODS® BDNF were added to wells of a 96-well plate and were spun down at 3000 g for 25 min. PBS was removed and the plate dried in a laminar flow cabinet. Aliquots of 100 µl RPMI supplemented with 10% BCS were added to each well. The plate was then incubated at 37° C., 5% $CO_2$. For the release time curve, medium from wells with 1e6 PODS® was collected at day 1, 2, 3, 4 and 7 after medium addition and stored at –20° C. For the dose response curve, medium was collected at day 4 after medium addition. Subsequent BDNF ELISA (Boster #EK0307) was performed according to the manufacturer's protocol.

Example 1. Modulation of Host Microenvironment by Sustained Growth Factor Delivery Enhances RGC Survival and Donor RGC Morphology Following Allotransplantation Retinal tissue was differentiated from Thy1-GFP mouse iPSC (C57Bl/6 background) over the course of 3 weeks in 3D-retinal organoids. RGCs were isolated by magnetic microbeads against CD90 at day 21 of development, Thy1-GFP+ RGCs were formulated at 20,000 cells in 2 ul with or without growth factor (GDNF/BDNF)-loaded polyhedrin-based particles (GF-PODS). Mice were injected with NMDA 1 week prior to intravitreal injection of donor RGCs to cause RGC death, and subsequently received either cells alone, cells+PODS, or PODS alone. To assess host retinal function electroretinography (ERG) were performed at 6 weeks and 6 months post-transplant. Donor cell identity was confirmed prior to transplant by qPCR, Immunohistochemistry and Flow Cytometry.

Figure 1A:
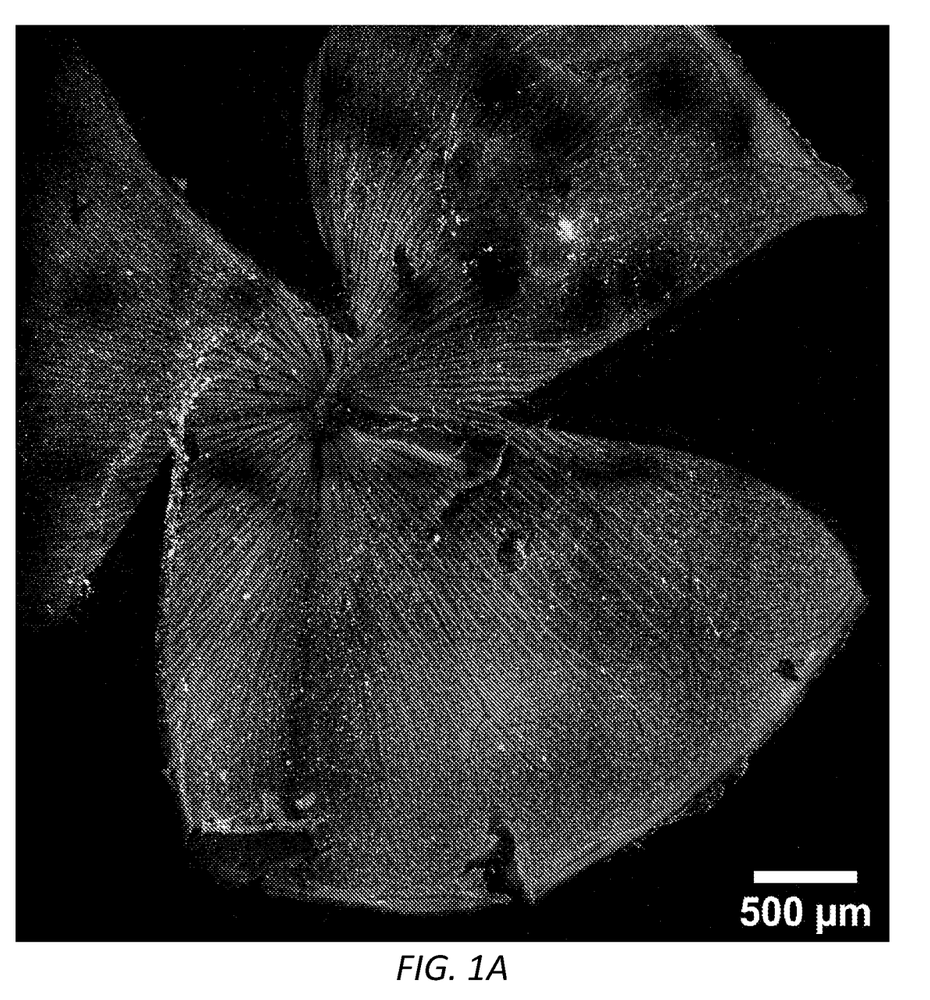
FIGS. 1A-B are fluorescent images showing that BDNF/GDNF-PODS cotreatment expanded RGC transplant coverage area. 1A, Thy1+ cells only. 1B, Thy1+ cells+BDNF/GDNF-PODS.
Figure 1B:
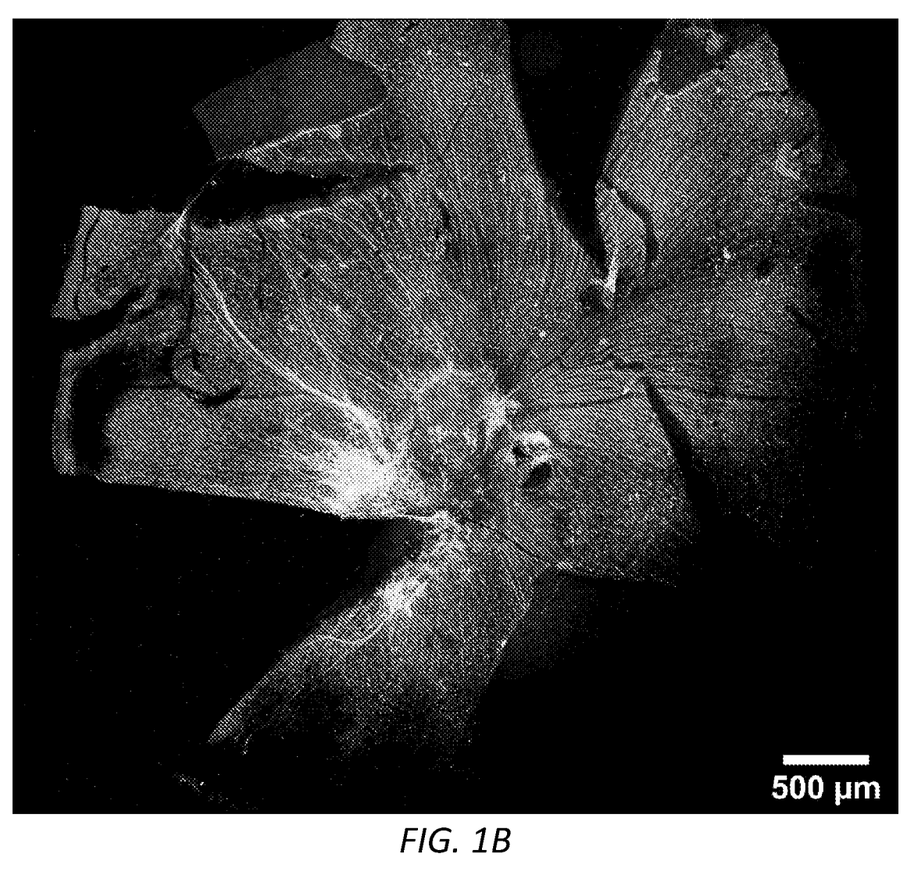
Figure 2A:
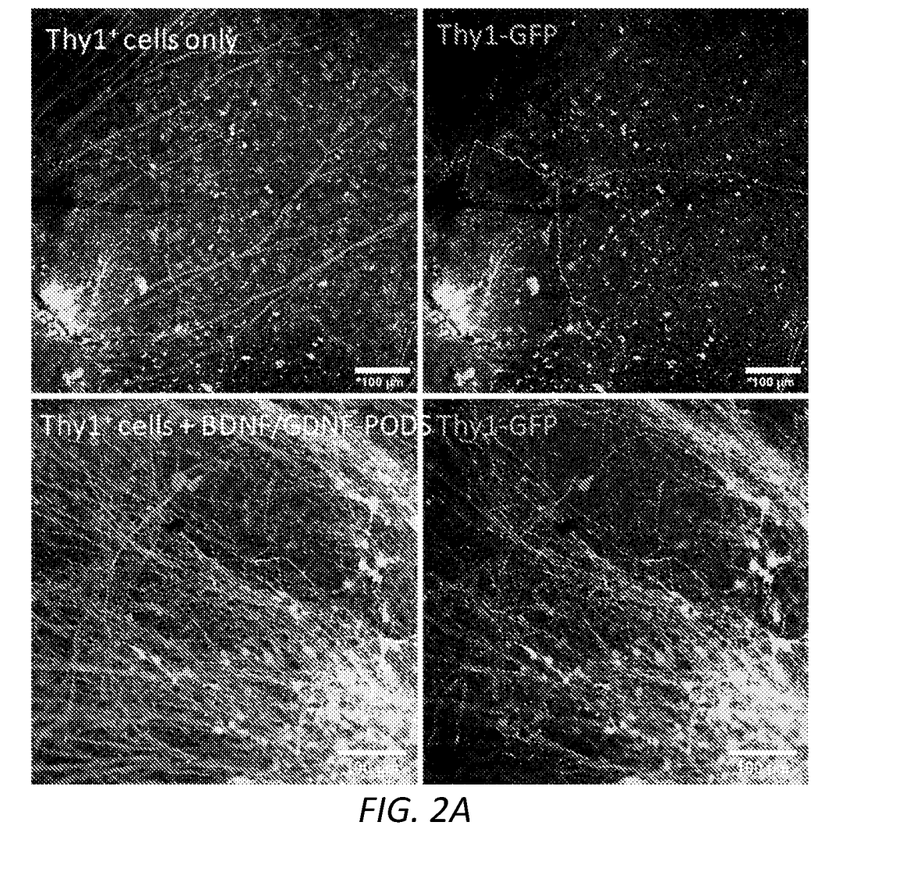
FIG. 2A is a fluorescent image showing that cotreatment improved neurite outgrowth.
Figure 2B:
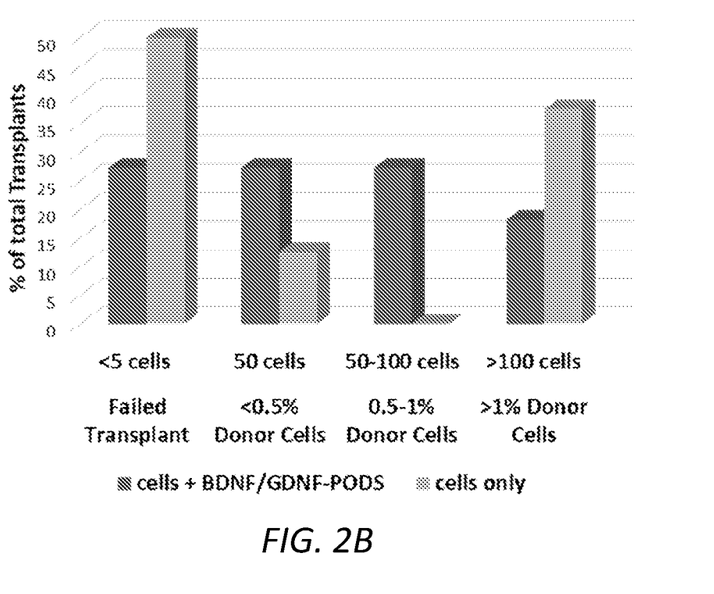
FIG. 2B is a graph showing improved donor RGC survival at 2 weeks post-Transplant in animals that received RGCs plus BDNF/GDNF-PODS.

Inclusion of BDNF/GDNF-PODS expanded the transplant coverage area (see FIGS. 1A-B, improved neurite outgrowth (FIG. 2A), and increased transplant success rate (73% as compared to 50% in the absence of the GF-PODS) (FIG. 2B).

Figure 3A:
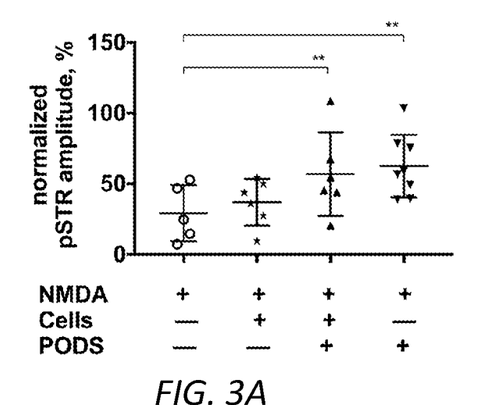
FIGS. 3A-B show that vision, as measured by ERG, was improved by both the GF-PODS along and the GF-PODS plus cells.
Figure 3B:
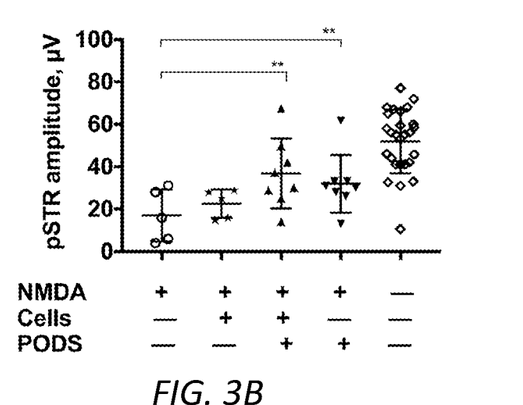

Thy1-GFP+ donor RGCs alone didn't rescue retinal function as assessed by ERG at 6 weeks post-transplantation in NMDA model of toxic optic neuropathy. Treatment with GF-PODS alone, or cells+GF-PODS, led to partial preservation of RGC function as measured by pSTR amplitude response at 6 weeks (32 uV in PODS only group vs 17 uV in control, FIG. 3B) as well as 6 months post-transplantation. Donor RGC axon outgrowth and morphology, including entry into the optic nerve head was enhanced by PODS co-treatment, proposing a benefit of co-treatment towards cell delivery.

Example 2. Time-Dependent Release of BDNF from BDNF-Polyhedrin Complexes

Figure 4A:
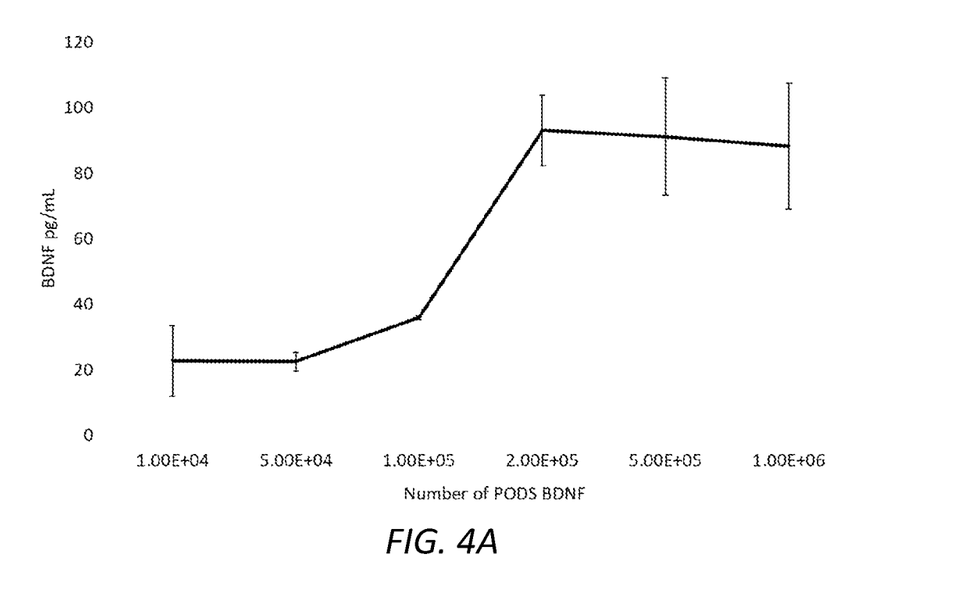
FIG. 4A shows dose-dependent release of BDNF from BDNF-PODS after 4 day incubation.
Figure 4B:
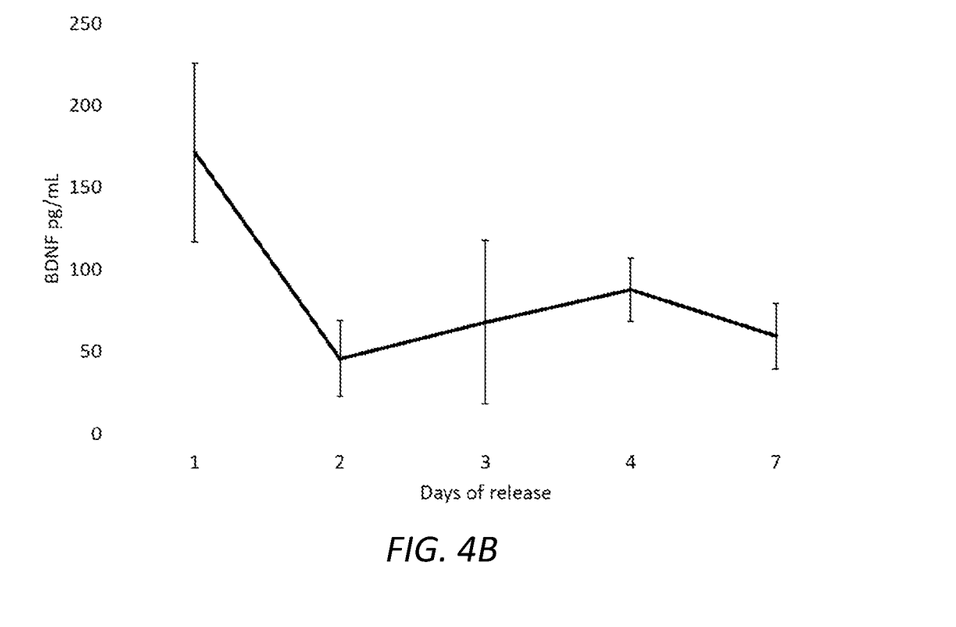
FIG. 4B shows time dependent release from 1e06 PODS® BDNF.

The release of BDNF from BDNF-polyhedrin complexes was measured by ELISA. The results, shown in FIGS. 4A and B, showed both time- and dose-dependence of release.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating glaucoma, Leber's hereditary optic neuropathy (LHON), toxic optic neuropathy, non-arteritic anterior ischaemic optic neuropathy (NAION), ischemic optic neuropathy, or retrograde degeneration associated with a pathology involving the Central Nervous System (CNS), the method comprising administering to an affected eye of a subject (a) a therapeutically effective amount of a composition comprising complexes of one or more growth factors attached to polyhedra comprising polyhedrin protein and (b) a population of donor retinal ganglion cells (RGCs).

2. The method of claim 1, wherein the growth factors comprise one, two, or all three of human Brain-derived neurotrophic factor (BDNF), Glial cell line-derived neurotrophic factor (GDNF), and/or Ciliary neurotrophic factor (CNTF).

3. The method of claim 1, wherein the growth factors have an N-terminal tag that facilitates attachment to the polyhedrin.

4. The method of claim 3, wherein the N-terminal tag comprises an N-terminus H1 helix of a polyhedrin protein or a region of a capsid protein Viral Protein 3 (VP3) of cytoplasmic polyhedrosis virus.

5. The method of claim 3, wherein the N-terminal tag is an H1-tag comprising Met Ala Asp Val Ala Gly Thr Ser Asn Arg Asp Phe Arg Gly Arg Glu Gln Arg Asn Ser Glu Gln Tyr Asn Tyr Asn Ser Ser (SEQ ID NO:1).

6. The method of claim 1, wherein the subject has early-stage glaucoma, LHON, toxic optic neuropathy, NAION, ischemic optic neuropathy, or retrograde degeneration associated with a pathology involving the CNS.

7. The method of claim 1, wherein the subject retains at least 30%, 40%, 50%, 60%, 70%, 80%, or 90% of the normal Retinal Nerve Fiber Layer (RNFL) thickness assessed by optical coherence tomography (OCT).

8. The method of claim 1, wherein the subject has late stage glaucoma, LHON, toxic optic neuropathy, NAION, ischemic optic neuropathy, or retrograde degeneration associated with a pathology involving the CNS.

9. The method of claim 1, wherein the subject has a Retinal Nerve Fiber Layer (RNFL) with a thickness of less than 10%, 20%, 30%, 40%, or 50%, of the normal RNFL thickness assessed by optical coherence tomography (OCT).

10. The method of claim 1, wherein the composition is administered by intravitreal or subretinal injection.

11. The method of claim 1, wherein the pathology of the CNS is Alzheimer's disease, Parkinson's disease, or demyelinating optic neuritis.

12. The method of claim 1, wherein the subject is human.

13. The method of claim 2, wherein the growth factors comprise human Brain-derived neurotrophic factor (BDNF) and Glial cell line-derived neurotrophic factor (GDNF).

14. The method of claim 1, wherein the donor RGCs are derived from induced pluripotent stem cells (iPSC) generated from cells from the subject or universal human leukocyte antigen (HLA) matched donor iPSC.

* * * * *

SEQUENCE LISTING

```
<160> NUMBER OF SEQ ID NOS: 4

<210> SEQ ID NO 1
<211> LENGTH: 28
<212> TYPE: PRT
<213> ORGANISM: Artificial Sequence
<220> FEATURE:
<223> OTHER INFORMATION: H1-tag

<400> SEQUENCE: 1

Met Ala Asp Val Ala Gly Thr Ser Asn Arg Asp Phe Arg Gly Arg Glu
1               5                   10                  15

Gln Arg Asn Ser Glu Gln Tyr Asn Tyr Asn Ser Ser
            20                  25

<210> SEQ ID NO 2
<211> LENGTH: 165
<212> TYPE: PRT
<213> ORGANISM: Homo sapiens
<220> FEATURE:
<221> NAME/KEY: MOD_RES
<222> LOCATION: (1)..(165)
<223> OTHER INFORMATION: BDNF amino acid

<400> SEQUENCE: 2

Met Ala Asp Val Ala Gly Thr Ser Asn Arg Asp Phe Arg Gly Arg Glu
1               5                   10                  15
```

```
Gln Arg Leu Phe Asn Ser Glu Gln Tyr Asn Tyr Asn Ser Lys Asn
            20                  25                  30

Ser Arg Pro Ser Thr Ser Leu Tyr Lys Lys Ala Gly Leu Met His Ser
        35                  40                  45

Asp Pro Ala Arg Arg Gly Glu Leu Ser Val Cys Asp Ser Ile Ser Glu
    50                  55                  60

Trp Val Thr Ala Ala Asp Lys Lys Thr Ala Val Asp Met Ser Gly Gly
 65                  70                  75                  80

Thr Val Thr Val Leu Glu Lys Val Pro Val Ser Lys Gly Gln Leu Lys
                85                  90                  95

Gln Tyr Phe Tyr Glu Thr Lys Cys Asn Pro Met Gly Tyr Thr Lys Glu
            100                 105                 110

Gly Cys Arg Gly Ile Asp Lys Arg His Trp Asn Ser Gln Cys Arg Thr
        115                 120                 125

Thr Gln Ser Tyr Val Arg Ala Leu Thr Met Asp Ser Lys Lys Arg Ile
    130                 135                 140

Gly Trp Arg Phe Ile Arg Ile Asp Thr Ser Cys Val Cys Thr Leu Thr
145                 150                 155                 160

Ile Lys Arg Gly Arg
                165

<210> SEQ ID NO 3
<211> LENGTH: 180
<212> TYPE: PRT
<213> ORGANISM: Homo sapiens
<220> FEATURE:
<221> NAME/KEY: MOD_RES
<222> LOCATION: (1)..(180)
<223> OTHER INFORMATION: GDNF amino acid

<400> SEQUENCE: 3

Met Ala Asp Val Ala Gly Thr Ser Asn Arg Asp Phe Arg Gly Arg Glu
 1               5                  10                  15

Gln Arg Leu Phe Asn Ser Glu Gln Tyr Asn Tyr Asn Ser Lys Asn
            20                  25                  30

Ser Arg Pro Ser Thr Ser Leu Tyr Lys Lys Ala Gly Leu Met Ser Pro
        35                  40                  45

Asp Lys Gln Met Ala Val Leu Pro Arg Arg Glu Arg Asn Arg Gln Ala
    50                  55                  60

Ala Ala Ala Asn Pro Glu Asn Ser Arg Gly Lys Gly Arg Arg Gly Gln
 65                  70                  75                  80

Arg Gly Lys Asn Arg Gly Cys Val Leu Thr Ala Ile His Leu Asn Val
                85                  90                  95

Thr Asp Leu Gly Leu Gly Tyr Glu Thr Lys Glu Glu Leu Ile Phe Arg
            100                 105                 110

Tyr Cys Ser Gly Ser Cys Asp Ala Ala Glu Thr Thr Tyr Asp Lys Ile
        115                 120                 125

Leu Lys Asn Leu Ser Arg Asn Arg Arg Leu Val Ser Asp Lys Val Gly
    130                 135                 140

Gln Ala Cys Cys Arg Pro Ile Ala Phe Asp Asp Asp Leu Ser Phe Leu
145                 150                 155                 160

Asp Asp Asn Leu Val Tyr His Ile Leu Arg Lys His Ser Ala Lys Arg
                165                 170                 175

Cys Gly Cys Ile
            180
```

```
<210> SEQ ID NO 4
<211> LENGTH: 200
<212> TYPE: PRT
<213> ORGANISM: Homo sapiens
<220> FEATURE:
<221> NAME/KEY: MOD_RES
<222> LOCATION: (1)..(200)
<223> OTHER INFORMATION: CNTF amino acid

<400> SEQUENCE: 4

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Ala Asp Gly Met Pro Val Ala Ser Thr Asp Gln Trp
     50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```